United States Patent [19]

Bollag

[11] Patent Number: 4,863,969

[45] Date of Patent: Sep. 5, 1989

[54] TREATMENT OF PREMALIGNANT LESIONS AND CERTAIN MALIGNANT TUMORS

[75] Inventor: Werner Bollag, Basel, Switzerland

[73] Assignee: Hoffmann-La Roche Inc., Nutley, N.J.

[21] Appl. No.: 164,293

[22] Filed: Mar. 4, 1988

Related U.S. Application Data

[63] Continuation of Ser. No. 874,932, Jun. 16, 1986, abandoned.

[30] Foreign Application Priority Data

Jun. 28, 1985 [CH] Switzerland ............... 2755/85

[51] Int. Cl.$^4$ ........................... A61K 31/015
[52] U.S. Cl. ................................ 514/765
[58] Field of Search ..................... 514/765

[56] References Cited

U.S. PATENT DOCUMENTS 4,588,750  5/1986  Boris .......................... 514/765

OTHER PUBLICATIONS

The Merck Manual, 1982, Merck & Co., Inc., Rahway, N.J., p. 2110.
Loeliger et al., Eur. J. Med. Chem.,-Chemica Therapeutica 15, No. 1, pp. 9-15 (1980).

*Primary Examiner*—Jerome D. Goldberg
*Attorney, Agent, or Firm*—John S. Saxe; George M. Gould; William H. Epstein

[57] ABSTRACT

1,2,3,4-Tetrahydro-1,1,4,4-tetramethyl-6-(α-methylstyryl)naphthalene possesses antihyperplastic, antimetaplastic, antineoplastic tumor-preventative and tumor-therapeutic properties and can accordingly be used in the treatment of precancerous or premalignant lesions as well as in the treatment of malignant tumors of epithelial and mesenchymal nature.

27 Claims, No Drawings

TREATMENT OF PREMALIGNANT LESIONS AND CERTAIN MALIGNANT TUMORS

This is a continuation of application Ser. No. 874-932 filed 6/16/86, now abandoned.

BACKGROUND OF INVENTION

This invention is directed to the treatment of premalignant lesions and malignant tumors. It has been known to utilize the compound 1,2,3,4-tetrahydro-1,1,4,4-tetramethyl-6-(alpha-methylstyryl)naphthalene which has the formula

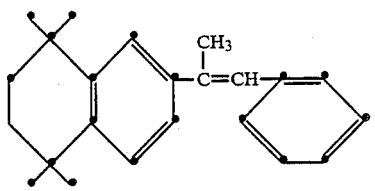

for the systemic and topical treatment or prevention of conditions caused by an increased sebum secretion, such as greasy hair, oily scalp, seborrhea and especially acne vulgaris. See U.S. Pat. No. 4,588,750, Boris, issued May 13, 1986. Prior to its discovery for use in the treatment or prevention of conditions caused by increased sebum secretion, the compound of formula I had been found biologically inactive in preliminary screening tests, see Rydell et al., Acta pharmacol. et toxicol., 51, 413–420 (1982); Kistler, Calcif Tissue Int. 33, 249–254 (1981) and Loeliger et al., Eur. J. Med. Chem.-Chimica Therapeutica, 15, No. 1, 9–15 (1980).

Retinoids play an essential role in controlling the normal differentiation of various tissues and are therefore important for controlling premalignant cell differentiation. It has even been found that retinoids can cause cellular repair of hyperplastic and anaplastic lesions caused by chemical carcinogens. Moreover, retinoid deficiency has been shown, in experimental animals, to enhance susceptibility to chemical carcinogenesis. Indeed, retinoids are essential for the normal cellular differentiation of epithelial cells where more than half of the total primary cancers develop in both men and women. These epithelial cells include the bronchi, trachea, breast, stomach, intestine, uterus, kidney, bladder, testis, prostate, pancreatic ducts and skin. In the absence of retinoids in the diet, normal cellular differentiation does not occur.

The developments in this field, which are summarized above, are discussed in an article entitled "Prevention of Chemical Carcinogenesis by Vitamin A and its Synthetic Analogs (Retinoids)", *Federation Proceedings*, 35, (May 1, 1976), 1332–1338, in which it is noted that it still remains a goal to find, for practical application to man and other mammals, highly effective synthetic retinoids that also have low toxicity and a high degree of tissue specificity against cancer at any particular organ site. See also the articles in the Fall, 1977, issue of *The Southern Research Institute Bulletin* (Volume 30, Number 2), pages 3–9 ("CHEMOPREVENTION OF CANCER—Steps Leading to Some Malignancies May Be Reversible" and "How Do Retinoids Work? Studies on Retinoic Acid-Binding Protein"). Other publications of interest in this field include "Biological Activity and Metabolism of the Retinoid Axerophthene (Vitamin A Hydrocarbon)", *Cancer Research* 38, 1734–1738, June 1978; and "Retinoids and Cancer Prevention: The importance of the Terminal Group of the Retinoid Molecule In Modifying Activity and Toxicity" in *Carcinogens: Identification and Mechanism of Action*, A. C. Griffin & C. R. Shaw, Editors, N.Y. Raven Press, 1978.

While retinoid-type compounds have been found to be effective in treating carcinomas, and inhibiting the progression of premalignant or precancerous lesions, many of these retinoids have high toxicity and produce deleterious adverse effects such as hypervitaminosis A. The toxicity and adverse effect profile of many of these retinoids make them unsuitable for use in the treatment and prevention of cancer at high dosage levels where their effects are greatest. Therefore, it is desired to provide a retinoid type compound which will exhibit at high dosages the tumor inhibiting effect of retinoids without the toxic manifestation or adverse effects generally associated with such retinoids.

SUMMARY OF INVENTION

In accordance with this invention, it has been discovered that the compound of formula I above when administered to mammals, exhibits the carcinoma-inhibiting effects of retinoids without any of the toxicity or adverse effects commonly associated with retinoids. This ability allows the compound of formula I above to be administered to mammals even at high dosages, without producing the toxicity or adverse effects such as hypervitaminosis A associated with retinoids.

In accordance with this invention, a method is provided for administering the compound of formula I to treat patients having premalignant lesions so as to retard the progression of these lesions into frank cancers. In accordance with another embodiment of this invention, the compound of formula I is administered to patients who have had a first treated primary malignancy, to inhibit the development of another primary malignancy in these patients. In accordance with another embodiment of this invention, a method is provided by administering the compound of formula I to treat tumors or carcinomas of mesenchymal or epithelial origin to retard the growth, development and progress of those tumors.

DETAILED DESCRIPTION

In accordance with this invention, it has been found that the compound of formula I possesses antihyperplastic, antimetaplastic, antineoplastic tumor-preventative and tumor-therapeutic properties without exhibiting the toxicity or adverse effects associated with retinoids. It has now been found that pathological conditions which involve the above properties can be effectively treated by administering the compound of formula I either systemically or topically.

In accordance with one embodiment of this invention, the compound of formula I when administered to mammals having premalignant lesions, i.e., precancerous lesions, retards the progression of the lesions. The compound of formula I controls the cellular differentiation of these premalignant or precancerous lesions and causes cellular repair of hyperplastic and anaplastic lesions. In this way, the development of these lesions into epithelial and mesenchymal carcinomas is prevented.

In treating premalignant or precancerous lesions to retard the progression of these lesions into carcinomas, the compound of formula I is administered either systemically or topically to patients affected by these lesions in an amount effective for retarding the progression of these lesions. The amount will be dependent on the amount and size of the lesions and on the requirement of the patient. In administering the compound of formula I to a patient for treating premalignant or precancerous lesions to retard the progression of these lesions into carcinomas, the compound of formula I is preferably administered orally at dosages of from 1 mg to about 50 mg per kilogram of body weight of the patient per day. This dosage can be administered as a single dosage or in several divided dosages proportioned in accordance with the direction of a physician. In general, however, a daily oral dose of about 1 mg to about 50 mg, preferably from about 3 mg to 15 mg per kilogram of body weight of the patient is generally utilized. In accordance with this invention, the compound of formula I can be administered in solid oral unit dosage forms, such as capsules, tablets, dragees, pills, powders, granulates and the like as well as liquid oral dosage forms such as solutions, syrups, suspensions, elixirs and the like. In general, the unit dosage forms should contain the compound of formula I in an amount of about 50 mg to 1,000 mg, preferably from about 150 to 500 mg. Of the unit oral dosage forms, capsules and tablets are especially preferred.

The compound of formula I is especially effective in treating premalignant or precancerous lesions of an epithelial and mesenchymal nature. The compound of formula I is effective in treating premalignant or precancerous lesions of the breast, skin, colon, bladder, esophagus, stomach, larynx, lung or oral cavity, particularly the mouth. In accordance with a preferred embodiment, the compound of formula I can be utilized to treat premalignant or precancerous lesions such as various leukoplakias, especially that of the mouth and tongue, as well as precancerous or premalignant lesions of the breast.

In accordance with another embodiment of this invention, the compound of formula I is administered for treating patients who have had a treated primary malignancy. It has been found that the administration of the compound of formula I to such patient inhibits both the recurrence of the primary malignancy and the development of a second primary malignancy. The first primary malignancy which occurs in a patient may occur as cancer of the breast or colon and this primary malignancy may be treated by removal through surgery or by other means. In accordance with this embodiment of the invention, the administration of the compound of formula I provides adjuvant therapy to prevent spread of the first malignancy to a different site. Furthermore, the compound of formula I also retards or inhibits the development of a second primary malignancy. Hence, the compound of formula I may be utilized to prevent a second primary malignancy where the first primary malignancy is a carcinoma or tumor of the breast, skin, colon, bladder, esophagus, stomach, larynx, lung, mouth etc. after the first primary malignancy has been treated such as through surgery or other means of removal. In accordance with this invention, it is found that the compound of formula I is effective for preventing a recurrence of the primary malignancy and the development of a second primary malignancy where the first primary malignancy is, for example, a carcinoma of the breast. In using the compound of formula I for adjuvant therapy to prevent the development of a secondary primary malignancy, the compound of formula I is administered either topically or systemically in the same amount as described with regard to treating premalignant or precancerous lesions. Generally, it is preferred to administer the compound for use in adjuvant therapy orally as described above.

In accordance with a further embodiment of this invention, the compound of formula I can be utilized to treat carcinomas or tumors of mesenchymal or epithelial origin to retard the development of these tumors. In accordance with the anti-carcinoma or anti-tumor properties of the compound of formula I, treatment of the tumors with the compound of formula I produces a regression in both the size and number of these tumors. In utilizing the compound of formula I as an anti-tumor agent, the compound of formula I is especially effective in retarding the development of tumor of the breast, skin, colon, bladder, esophagus, stomach, larynx, lung or mouth. Among the carcinomas against which this compound is especially effective is carcinoma of the breast. The compound of formula I can be administered to patients in the manner described above in connection with treating patients having premalignant or precancerous lesions. In carrying out this anti-tumor treatment, it is generally preferred to administer the compound of formula I at the dosages set forth above.

For the treatment given above, the compound of formula I is administered either systemically or topically as a composition containing the compound of formula I and a pharmaceutically acceptable carrier compatible with said compound. In preparing such composition, any conventional pharmaceutically acceptable carrier can be utilized. When the drug is administered orally, it is generally administered at regular intervals, conveniently at mealtimes or once daily. It has been established that the compound of formula I is relatively non-toxic when given intraperitoneally and when given orally.

Examples of conditions involving premalignant and precancerous lesions or tumors which are effectively treated with the compound of formula I are actinic keratoses, arsenic keratoses, xeroderma pigmentosum, Bowen's disease, hyperkeratoses, pachydermias, leukoplakias, metaplasias, dysplasias and papillomas of mucous membranes, e.g. of the mouth, tongue, pharynx and larynx, precancerous changes of the bronchial mucous membrane such as metaplasias and dysplasias (especially frequent in heavy smokers and people who work with asbestos and/or uranium), dysplasias and leukoplakias of the cervix uteri and vulva, kraurosis vulvae, precancerous changes of the bladder, e.g. metaplasias, dysplasias and papillomas, as well as polyps of the intestinal tract. Examples of tumors or carcinomas, of semi-malignant or malignant nature, of the epithelial or mesenchymal origin which are effectively treated by the compound of formula I are breast tumors, skin tumors, e.g. basal cell carcinomas, bladder tumors, e.g. superficial bladder carcinomas, colon tumors, esophageal tumors, stomach tumors, laryngeal tumors, lung tumors, B- and T-cell lymphomas, chondrosarcomas and osteosarcomas.

The treatment of precancerous lesions and malignant tumors of epithelial and mesenchymal nature can be effected with the compound of formula I alone or in combination with other measures such as surgery, radiation therapy, hormone therapy or treatment with standard chemotherapy (cytostatics and cytotoxins) or other biological response modifiers (interferons, interleukins, or other lymphokines).

The (E)-isomer, i.e. 1,2,3,4-tetrahydro-1,1,4,4-tetramethyl-6-[(E)-alpha-methylstyryl]naphthalene (compound Ia), is preferred for the use in accordance with the invention, although it is foreseen that the (Z)-isomer, i.e. 1,2,3,4-tetrahydro-1,1,4,4-tetramethyl-6-[(Z)-alpha-methylstyryl]naphthalene (compound Ib), can likewise be used in the scope of the present invention, alone or in combination with the preferred (E)-isomer Ia.

For the treatment in accordance with this invention, the compound of formula I is administered systemically or topically, preferably systemically, especially enterally and particularly orally.

The dosage in the case of systemic administration varies in accordance with the requirements of the individual patient as determined by the treating physician. In general, however, a daily oral dosage of about 1 mg to about 50 mg, preferably of about 3 mg to about 15 mg, per kg body weight of the patient should be used. The dosage can be administered as a single dosage or in several divided dosages apportioned in accordance with a dosage plan as determined by the physician in accordance with the requirements of the patient.

As administration forms for systemic administration there are the usual solid or liquid dosage forms, e.g. suppositories or as solid oral dosage forms capsules, tablets, dragees, pills, powders, granulates and the like, as liquid oral dosage forms solutions, syrups, suspension, elixirs and the like and as parenteral dosage forms infusion or injection solutions which can be injected intravenously or intramuscularly.

It is possible in the scope of the present invention to incorporate the compound of formula I in the enteral or parenteral dosage form in any amount which is suitable for systemic administration. It is, however, preferred to manufacture preparations which contain the active substance in accordance with the invention in an amount of from about 50–1000 mg, preferably of about 150–500 mg. The manufacture of capsules and tablets is especially preferred.

Solutions, lotions, suspensions, salves, creams, gels, micronized powders, aerosols and the like are suitable for topical administration. These preparations conveniently contain from about 0.1 to about 10 wt.%, preferably from about 0.5 to about 5 wt.%, of the compound of formula I calculated on the total weight of the preparation.

The manufacture of the above-mentioned systemic and topical forms of use can be carried out in the usual manner, e.g. on the basis of the Examples hereinafter.

EXAMPLE 1

Hard gelatine capsules containing the following ingredients can be manufactured:

| Ingredients | mg/capsule |
| --- | --- |
| 1. Spray-dried powder containing 75% of compound Ia | 200 |
| 2. Sodium dioctyl sulphosuccinate | 0.2 |
| 3. Sodium carboxymethylcellulose | 4.8 |
| 4. Microcrystalline cellulose | 86.0 |
| 5. Talc | 8.0 |
| 6. Magnesium stearate | 1.0 |
| Total | 300 |

Procedure

The spray-dried powder, which is based on the active substance, gelatine and microcrystalline cellulose and which has an average particle size of the active substance of less than 1μ (measured of means of autocorrelation spectroscopy), is moistened with an aqueous solution of sodium carboxymethylcellulose and sodium dioctyl sulphosuccinate and kneaded. The resulting mass is granulated, dried and sieved, and the granulate obtained is mixed with microcrystalline cellulose, talc and magnesium stearate. The powder is filled into size 0 capsules.

EXAMPLE 2

Tablets containing the following ingredients can be manufactured:

| Ingredients: | mg/tablet |
| --- | --- |
| 1. Compound Ia as a finely milled powder | 500 |
| 2. Lactose powd. | 100 |
| 3. Maize starch white | 60 |
| 4. Povidone K30 | 8 |
| 5. Maize starch white | 112 |
| 6. Talc | 16 |
| 7. Magnesium stearate | 4 |
| Total | 800 |

Procedure

The finely milled substance is mixed with powd. lactose and white maize starch. The mixture is moistened with an aqueous solution of Povidone K30 and kneaded and the resulting mass is granulated, dried and sieved. The granulate is mixed with white maize starch (2nd portion), talc and magnesium stearate and pressed to tablets of suitable size.

EXAMPLE 3

Soft gelatine capsules containing the following ingredients can be manufactured:

| Ingredients | mg/capsule |
| --- | --- |
| 1. Compound Ia | 50 |
| 2. Triglyceride | 450 |
| Total | 500 |

Procedure 10 g of compound Ia are dissolved in 90 g of medium-chain triglyceride with stirring, inert gasification and protection from light. This solution is processed as the capsule fill mass by a contact manufacturer to soft gelatine capsules containing 50 mg of active substance.

EXAMPLE 4

A fatty salve containing the following ingredients can be manufactured:

| Ingredients: | |
| --- | --- |
| 1. Compound Ia, finely milled | 3.0 g |
| 2. Paraffin oil, internally viscous | 30.0 g |
| 3. Lunacera M | 15.0 g |
| 4. Castor oil, hardened | 5.0 g |
| 5. Vaseline, white ad | 100 g |

Procedure

All adjuvants are mixed in the warm and stirred while cooling to room temperature. The active substance is homogeneously mixed with the mixture obtained in this manner in the cold under protection from light.

EXAMPLE 5

A fatty cream containing the following ingredients can be manufactured:

| Ingredients: | | |
|---|---|---|
| 1. Compound Ia, finely milled | 3.0 g | |
| 2. Vaseline, white | 30.0 g | |
| 3. Wax, white | 5.0 g | fatty phase |
| 4. Paraffin oil, internally viscous | 20.0 g | |
| 5. Dehymuls E | 9.0 g | |
| 6. Benzoic acid | 0.2 g | aqueous phase |
| 7. Demineralized water ad | 100.0 g | |

Procedure

Fatty phase and aqueous phase are processed to a fatty cream. The active substance is homogeneously mixed with this fatty cream at room temperature under protection from light.

EXAMPLE 6

A vanishing cream (o/w emulsion type) containing the following ingredients can be manufactured:

| Ingredients: | | |
|---|---|---|
| 1. Compound Ia, finely milled | 3.0 g | |
| 2. Glycerine monostearate | 17.0 g | |
| 3. Deltyl extra | 4.0 g | fatty phase |
| 4. Tween 60 | 4.0 g | |
| 5. Span 60 | 4.0 g | |
| 6. Silicon oil AR 20 | 2.0 g | |
| 7. Propylene glycol | 10.0 g | |
| 8. Benzoic acid, pure | 0.2 g | aqueous phase |
| 9. Demineralized water ad | 100.0 g | |

Procedure

The fatty phase and aqueous phase are processed to a cream. The active substance is homogeneously mixed with this cream at room temperature under protection from light.

EXAMPLE 7

A hydrophilic gel containing the following ingredients can be manufactured:

| Ingredients: | |
|---|---|
| 1. Compound Ia, finely milled | 3.0 g |
| 2. Carbopol 940 | 2.5 g |
| 3. Propylene glycol | 50.0 g |
| 4. Ethanol, 94% ad | 100.0 g |

Procedure

The active substance is incorporated in the polypropylene glycol/ethanol (94%) mixture under protection from light. Carbopol 940 is stirred in until gelling is complete.

EXAMPLE 8

A lotion containing the following ingredients can be manufactured:

| Ingredients: | |
|---|---|
| 1. Compound Ia, finely milled | 3.0 g |
| 2. Carbopol 934 | 0.6 g |
| 3. Sodium hydroxide q.s. ad pH 6 | |
| 4. Ethanol, 94% | 50.0 g |

-continued

| Ingredients: | |
|---|---|
| 5. Demineralized water ad | 100.0 g |

Procedure

The active substance is incorporated into the ethanol, (94%)/water mixture under protection from light. Carbopol 934 is stirred in until gelling is complete and the pH value is adjusted with sodium hydroxide.

The therapeutic and prophylactic activity of the compound of formula I in the case of precanceroses and tumors of epithelial and mesenchymal nature can be concluded from the following experiments:

(A) The activity of compound Ia with respect to the prevention of chemically-induced breast tumors was determined according to the following procedure. Female Sprague-Dawley rats were used in this experiment. The experimental animals were kept under temperature-controlled and light-controlled conditions and had free access to drinking water and feed. At the age of 50 days 15 mg of dimethyl-benz(a)anthracene dissolved in arachis oil were administered to each rat by means of a probang. The treatment with compound Ia began 1 day after the administration of the carcinogen. The body weight of the experimental animals was recorded and the tumors were palpated weekly and measured with a vernier caliper. The volumes were calculated according to the formula $D/2 \cdot d^2$ in which D represents the larger diameter of the tumor ellipsoid and d represents the smaller diameter of the tumor ellipsoid. After 11 weeks the experiment was terminated and evaluated. In this experiment there were used in addition to 30 control animals, which received exclusively normal feed, the following three groups of experimental animals:

1. 33 rats to which were administered daily 30 mg/kg of compound Ia mixed with the feed.
2. 36 rats to which were administered daily 90 mg/kg of compound Ia mixed with the feed.
3. 33 rats to which were administered daily 270 mg/kg of compound Ia mixed with the feed.

The feed mixture was adjusted weekly according to the body weight and the total food intake. The results are compiled in Table I.

TABLE I

| Daily oral dosage | % tumor-bearing rats | Average number of tumors per rat | Average tumor volume per rat in mm$^3$ |
|---|---|---|---|
| Control animals | 79.3 (100%) | 3.7 (100%) | 6335 (100%) |
| 30 mg/kg | 69.6 (88%) | 3.0 (81%) | 4904 (77%) |
| 90 mg/kg | 63.8 (80%) | 1.8 (48%) | 2879 (45%) |
| 270 mg/kg | 39.3 (50%) | 0.7 (18%) | 543 (9%) |

(B) The activity of compond Ia on tumors was, furthermore, determined on the transplantable chondrosarcoma of the rat according to the following method. The solid tumor of a donor animal was finely minced and suspended in phosphate-buffered sodium chloride solution. 0.5 ml of the 30% tumor suspension was implanted subcutaneously into albino rats. The experiment was commenced when the experimental animals exhibited a tumor area (product from the largest and smallest diameter) of approximately 1200–1300 mm$^2$ (3–4 weeks after the implantation). Each treatment group embraced 7 rats. Suspensions of compound Ia in arachis oil were administered orally five times per week for 4 weeks. The tumor areas were determined on days 1, 15 and 29. The largest (D) and the smallest (d) diameter of the tumors were determined with the aid of a vernier caliper and the product D·d was determined. The change in this area size was calculated in percentages. The results are compiled in Table II.

TABLE II

| Treatment | Tumor area in mm² | | |
|---|---|---|---|
| | Day 1 | Day 15 after the commencement of treatment | Day 29 |
| Control animals | 1199 | 2880 (+140%) | 5926 (+394%) |
| Compound Ia 400 mg/kg p.o. | 1300 | 1416 (+9%) | 1694 (+30%) |

(C) The antimetaplastic activity of compound Ia was determined in rats according to the following method. Female Holtzmann rats weighing approximately 100 g were ovarectomized under Thiogenal narcosis after an adaptation period of 8 days and were used in the experiment after a further 14 days. In each case two animals were placed in a cage and had free access to feed which contained approximately 2000 IU of analytically determined vitamin A. Prior to the oral administration of the test compound the animals were treated subcutaneously each day for 6 successive days with the hormone mixture of 1 µg of estradiol benzoate and 250 µg of testosterone propionate dissolved in 0.1 ml of sesame oil. The parenteral hormone administration led to the formation of a clear granular stage in the vaginal smear, i.e. a squamous metaplasia. 2 days after the oral administration of the test substance the result of the reaction was again read off on the vaginal epithelium. The area method according to Behrens and Karber was employed to calculate the average effective dosages. The results are compiled in Table III.

TABLE III

| Compound | Antimetaplastic effect | Relative activity |
|---|---|---|
| all-Trans vitamin A acid | 35.7 µg | 100% |
| Compound Ia | 53.6 µg | 66.6% |

As can be concluded from the above results, an average protective dosage of 35.7 µg was ascertained for the standard preparation, while the protective dosage for the test compound was 53.6 µg. Accordingly, an epithelium protection effect (=anti-metaplastic effect) reduced by the factor 0.67 was found for compound Ia compared with the chosen standard preparation all-trans vitamin A acid.

Since metaplasia can be regarded as the first stage in the transformation of normal tissue into premalignant and malignant tissue, on the basis of the metaplasia-preventing activity of a specific compound certain predictions can be made with respect to the tumor-preventing activity of this compound.

(D) The activity of compound Ia on chemically-induced precancerous tissue changes was, furthermore, determined in vitro according to the following method. In this experiment prostate glands of mice and trachea of rats cultivated in organ cultures served as the experimental models. In tissues of organ cultures carcinogenic substances bring about after a short period precancerous changes in the form hyperplasias as well as metaplasias and dysplasias. Retinoids, which are administered simultaneously with the carcinogenic compounds or after these, prevent the hyperplasia or metaplasia and dysplasia or even cause these to regress.

The prostate glands consist of alveoli lined with one row of secretory cells and separated by a thin connective tissue. They were removed from mice aged 3–5 months and cut into lobules of approximately $1.5 \times 1.5 \times 2.0$ mm. At least six of these lobules were placed on filter paper and transferred on a metal lattice into small culture chambers. Two of these culture chambers were enclosed in a Petri dish lined with a moist filter paper. The culture chambers were filled with nutrient medium up to the height of the lattice so that the explants were moistened well with the nutrient medium, but were not immersed in this. At the nutrient medium there was used customary Medium 199 supplemented by the addition of 15% serum from newly born calves. The carcinogen (3-methylcholanthrene) was added to this prior to the incubation in a concentration of 4–5 µg/ml of nutrient medium. The cultures were then incubated at 37.5° C. During the incubation they were kept in a Macintosh flask which was gassed with a mixture of 5% $CO_2$ + 95% oxygen. In a first series of experiments the carcinogen and compound Ia were combined and the tissue was cultivated for 10–12 days. In a second series the explants were pre-treated with the carcinogen for 10–12 days and thereafter placed in a nutrient medium, which only contained compound Ia, for 4–7 days. The concentration of compound Ia lay in the range of $10^{-9}$ to $10^{-6}$ Mol.

The activity of compound Ia is quantified by counting the normal and hyperplastic alveoli in sections of the explant. The results are expressed in percentages of hyperplastic alveoli of the total number of alveoli, for example 120 hyperplastic alveoli out of a total of 200 correspond to 60%. In explants treated with retinoids the percentage is usually small. For example, explants treated with a carcinogen exhibited 60% and explants treated with a retinoid exhibited 20%. The percentage of hyperplastic alveoli is reduced to 20/60=33%.

Trachea of rats are cultivated in the same manner and treated with dimethylbenzanthracene as the carcinogen. The mitotic index serves as the parameter of the hyperplasia. With retinoid the mitotic index and the hyperplasias, respectively, are smaller. The results are compiled in Tables IV (prostate) and V (trachea).

TABLE IV

| Prostate (mouse)/hyperplasia induced by methylcholanthrene | | | |
|---|---|---|---|
| Simultaneous treatment with compound Ia | | Subsequent treatment with compound Ia | |
| Methylcholanthrene (47% hyperplastic alveoli) | 100% | Methylcholanthrene (65%) hyperplastic alveoli) | 100% |
| Compound Ia | | | |
| $10^{-9}$M | 90% | | 100% |
| $10^{-8}$M | 60% | | 98% |
| $10^{-7}$M | 46% | | 94% |
| $10^{-6}$M | 25% | | 54% |

TABLE V

| Trachea (rats)/hyperplasia induced by dimethylbenzanthracene | |
|---|---|
| Simultaneous treatment with compound Ia | Subsequent treatment with compound Ia |
| Dimethylbenzanthracene | Di- |

TABLE V-continued

| Trachea (rats)/hyperplasia induced by dimethylbenzanthracene | | | |
|---|---|---|---|
| Simultaneous treatment with compound Ia | | Subsequent treatment with compound Ia | |
| (mitotic index 2.6) compound Ia | 100% | methylbenzathracene (mitotic index 3.1) | 100% |
| $10^{-9}$M | 104% | | 75% |
| $10^{-8}$M | 46% | | 74% |
| $10^{-7}$M | 46% | | 70% |
| $10^{-6}$M | 54% | | 45% |

It is known that 1,2,3,4tetrahydro-1,1,4,4-tetramethyl-6-[(E)-alpha-methylstyryl]naphthalene Ia is well tolerated and that no toxic symptoms appear in the therapeutically indicated dosages. Thus, compound Ia does not exhibit, in particular, any hypervitaminosis A phenomena (e.g. no manifestations on skin and mucous membranes) and is non-teratogenic and not irritating to the skin. Over and above this it has been shown that compound Ia, as a sole therapeutically active retinoid, brings about no increase in the lipid value in blood plasma, but on the contrary even possesses a lipid-lowering activity.

In order to detect this activity a dosage of compound Ia was administered five times per dosage to 5 male and 5 female albino rats weighing approximately 150 g by means of a probang within 2 days in intervals of in each case 18 and 6 hours. 18 hours after the last application 1-1,2 ml of blood plasma were removed retroorbitally from the experimental animals. The triglyceride value was determined by enzymatic cleavage of the triglyceride with subsequent determination of the resulting glycerine (colour reaction) by means of Periodchrom triglyceride GPO-PAP. The results are compiled in Table VI.

TABLE VI

| | Male rats | Female rats |
|---|---|---|
| Control animals | 201 ± 39 mg/100 ml | 69 ± 28 mg/100 ml |
| Compound of formula Ia | | |
| 10 mg/kg | 158 ± 56 mg/100 ml | 56 ± 25 mg/100 ml |
| 100 mg/kg | 173 ± 18 mg/100 ml | 72 ± 18 mg/100 ml |
| 1000 mg/kg | 41 ± 19 mg/100 ml | 30 ± 8 mg/100 ml |

I claim:

1. A method for treating patients having premalignant or precancerous lesions whle are leukoplakias or dysplasias to retard the progression of these lesions into carcinomas comprising administering to said patient a composition containing the compound 1,2,3,4-tetrahydro-1,1,4,4-tetramethyl-6-(alpha-methylstyryl)naphthalene, said compound being administered in an amount effective to treat said lesions.

2. The method of claim 1 wherein said compound is 1,2,3,4-tetrahydro-1,1,4,4-tetramethyl-6-[(E)-alpha-methylstyryl]naphthalene.

3. The method of claim 1 wherein said composition is administered orally.

4. The method of claim 3 wherein compound is administered at a daily amount dose of from 1 mg to 50 mg per kg body weight.

5. The method of claim 4 wherein said lesions are leukoplakias of the oral cavity.

6. The method of claim 4 wherein said lesions are precancerous epithelial lesions of the breast.

7. The method of claim 4 wherein said composition is administered at a daily dose of from 3 mg to 15 mg per kg body weight.

8. The method of claim 7 wherein said composition is administered in an oral unit dosage form containing 150 mg to 500 mg of the compound.

9. The method of claim 8 wherein said oral unit dosage form is a capsule or tablet.

10. A method for treating patients who have had a treated primary malignancy which is an epithelial carcinoma to inhibit the development of second primary malignancy or a recurrence of said treated primary malignancy comprising administering to said patients a composition containing the compound 1,2,3,4-tetrahydro-1,1,4,4-tetramethyl-6-(alpha-methylstyryl)naphthalene, said compound being administered in an amount effective to inhibit the development of a second primary malignancy or recurrence of said treated primary malignancy.

11. The method of claim 10 wherein said compound is 1,2,3,4-tetrahydro-1,1,4,4-tetramethyl-6-[(E)-alpha-methylstyryl]naphthalene.

12. The method of claim 10 wherein said composition is administered orally.

13. The method of claim 12 wherein said compound is administered at a daily dose of from 1 mg to 50 mg per kg body weight.

14. The method of claim 13 wherein said treated primary malignancy is an epithelial carcinoma of the breast, skin, colon, bladder, esophagus, stomach, larynx, lung or oral cavity.

15. The method of claim 14 wherein said treated primary malignancy is a carcinoma of the breast.

16. The method of claim 13 wherein said composition is administered at a daily dose of 3 mg to 15 mg per kg body weight.

17. The method of claim 16 wherein said composition is administered in an oral unit dosage form containing 150 mg to 500 mg of the compound.

18. The method of claim 17 wherein said oral unit dosage form is a capsule or tablet.

19. A method for treating tumors of epithelial origin in patients to retard the development of these tumors comprising administering to said patient a composition containing the compound 1,2,3,4-tetrahydro-1,1,4,4-tetramethyl-6-(alpha-methylstyryl)naphthalene, said compound being administered in an amount effective to retard the development of said tumors.

20. The method of claim 19 wherein said compound is 1,2,3,4-tetrahydro-1,1,4,4-tetramethyl-6-[(E)-alphamethylstyryl]naphthalene.

21. The methodof claim 19 wherein said composition is administered orally.

22. The method of claim 21 wherein said compound is administered at a daily dose of from 1 mg to 50 mg per kg body weight.

23. The method of claim 22 wherein said tumors are selected from the group consisting of epithelial tumors of the breast, skin, colon, bladder, esophagus, stomach, larynx, lung or oral cavity.

24. The method of claim 23 wherein said tumor is an epithelial carcinoma of the breast.

25. The method of claim 22 wherein said compound is administered at a daily dose of from 3 mg to 15 mg per kg body weight.

26. The method of claim 25 wherein said composition is administered in an oral unit dosage form containing 150 mg to 500 mg of the compound.

27. The method of claim 26 wherein said oral unit dosage form is a capsule or tablet.

* * * * *

UNITED STATES PATENT AND TRADEMARK OFFICE
CERTIFICATE OF CORRECTION

PATENT NO. : 4,863,969

DATED : September 5, 1989

INVENTOR(S) : WERNER BOLLAG

It is certified that error appears in the above-identified patent and that said Letters Patent is hereby corrected as shown below:

COLUMN 11, LINE 50 "whle" should be which

Signed and Sealed this

Fourteenth Day of August, 1990

*Attest:*

HARRY F. MANBECK, JR.

*Attesting Officer*  *Commissioner of Patents and Trademarks*